United States Patent
Xu et al.

(10) Patent No.: US 10,294,196 B2
(45) Date of Patent: May 21, 2019

(54) PROCESS FOR THE SYNTHESIS OF INTERMEDIATES USEFUL FOR PREPARING 1,3,4-TRIAZINE DERIVATIVES

(71) Applicant: FMC Corporation, Philadelphia, PA (US)

(72) Inventors: Sheng Xu, Shanghai (CN); YiHui Xu, Shanghai (CN)

(*) Notice: Subject to any disclaimer, the term of this patent is extended or adjusted under 35 U.S.C. 154(b) by 0 days.

(21) Appl. No.: 15/777,314

(22) PCT Filed: Nov. 14, 2016

(86) PCT No.: PCT/US2016/061842
§ 371 (c)(1),
(2) Date: May 18, 2018

(87) PCT Pub. No.: WO2017/087323
PCT Pub. Date: May 26, 2017

(65) Prior Publication Data
US 2018/0334427 A1    Nov. 22, 2018

Related U.S. Application Data

(60) Provisional application No. 62/256,825, filed on Nov. 18, 2015.

(51) Int. Cl.
*C07C 249/16*    (2006.01)

(52) U.S. Cl.
CPC .................... *C07C 249/16* (2013.01)

(58) Field of Classification Search
CPC ..................................... C07C 249/16
See application file for complete search history.

(56) References Cited

U.S. PATENT DOCUMENTS

| | | |
|---|---|---|
| 5,436,240 A | 7/1995 | Moon et al. |
| 5,491,245 A | 2/1996 | Gruning et al. |
| 9,701,662 B2 * | 7/2017 | Mitchell .............. C07D 403/12 |
| 2008/0114196 A1 | 5/2008 | Kutschera et al. |
| 2012/0004443 A1 | 1/2012 | Tani |

FOREIGN PATENT DOCUMENTS

| | | |
|---|---|---|
| DE | 3345268 A1 | 12/1983 |
| EP | 167053 A1 | 6/1985 |
| EP | 330203 A1 | 2/1989 |
| JP | 27004157 B | 10/1952 |
| WO | 2007/044084 A2 | 4/2007 |
| WO | 2012002096 A1 | 1/2012 |
| WO | 2014/031971 A1 | 2/2014 |
| WO | 2015/128424 A1 | 9/2015 |

OTHER PUBLICATIONS

Kumar et al, International Journal of ChemTech Research, Synthesis, Antiinflammatory and Antimicrobial Activities of New Hydrazone and Quinoxaline derivatives, 2009, 1(4), pp. 1177-1181. (Year: 2009).*
International Search Report from PCT/US16/61842 dated Jan. 25, 2017.
Palmer, C. S. and McWherter, P. W., "Ethyl Bromomalonate", Organic Syntheses, Coll. vol. 1, p. 245 (1941).
Dox, A. W., "Ethyl Oxomalonate", Organic Syntheses, Coll vol. 1, p. 266 (1941).
A. N. Nesmeyanov Institute of Organometallic Compounds, Academy of Sciences of the USSR, Translated from Zhurnal Prikladnoi Khimii (Russian Journal of Applied Chemistry), vol. 58, No. 11, p. 2504-2508, Nov. 1985.

* cited by examiner

*Primary Examiner* — Paul A Zucker
(74) *Attorney, Agent, or Firm* — Reed A Coats

(57) ABSTRACT

A process for the synthesis of 1,3-diethyl 2-(2-methylhydrazinylidene)propanedioate comprising the step of: reacting 2-halosubstituted diethyl malonate or mixtures of 2-halo-substituted diethyl malonates with methylhydrazine or the salt thereof in the presence of an acid catalyst is disclosed. 1,3-diethyl 2-(2-methylhydrazinylidene)propanedioate is an intermediate useful for preparing 1,3,4-triazines.

13 Claims, No Drawings

PROCESS FOR THE SYNTHESIS OF INTERMEDIATES USEFUL FOR PREPARING 1,3,4-TRIAZINE DERIVATIVES

TECHNICAL FIELD

The present invention relates to the synthesis of the intermediates useful for the preparation of 1,3,4-triazine derivatives, more specifically the intermediate is 1,3-diethyl 2-(2-methylhydrazinylidene)propanedioate.

BACKGROUND 1,3,4-triazine-based derivatives are a subgroup of the triazines and many of them exhibit herbicidal activity and have been synthesized and widely used to protect crop against weeds. More recently, a novel 1,3,4-triazine based derivative was reported by SHIBAYAMA, Atsushi, et al in WO 2012/002096 A.

1,3-diethyl 2-(2-methylhydrazinylidene)propanedioate (the "DMP") is an important intermediate compound for the preparation of the 1,3,4-triazine based derivatives and that is used mainly to form the 1,3,4-triazine ring. With respect to the preparation of the DMP, the diethyl malonate is often used as a starting raw material and first converted to diethyl ketomalonate. Then, the resultant diethyl ketomalonate is to react with methylhydrazine to obtain DMP. One shortcoming of this process is the involvement of the conversion from diethyl malonate to diethyl ketomalonate, which by nature is a hazardous oxidation reaction and involves undesired complicated side reactions. Thus, there is still a strong need for the provision of a more efficient and effective process for the preparation of the DMP in avoidance of the stated shortcoming.

SUMMARY

That need is fulfilled by the present invention. The present invention provides a novel process for the synthesis of 1,3-diethyl 2-(2-methylhydrazinylidene)propanedioate. The present process uses 2-halo-substituted diethyl malonate (referred to herein as "-DEM") and does not need convert diethyl malonate to diethyl ketomalonate. Therefore, the unwanted hazardous oxidation and complicated side reaction are avoided.

In one aspect, the present invention provides a process for the synthesis of 1,3-diethyl 2-(2-methylhydrazinylidene) propanedioate by reacting 2-halo-substituted diethyl malonate with methylhydrazine or the salt thereof. In one embodiment, 2-halo-substituted diethyl malonate is selected from the group consisting of diethyl 2-bromomalonate, diethyl 2,2-dibromomalonate, diethyl 2-chloromalonate, diethyl 2,2-dichloromalonate, and any mixtures thereof.

In another aspect, the present invention provides a process for the synthesis of 1,3-diethyl 2-(2-methylhydrazinylidene) propanedioate, comprising: reacting 2-halo-substituted diethyl malonate with methylhydrazine or the salt thereof in a solvent selected from the group consisting of methanol, ethanol, 1-propanol, isopropyl alcohol, acetonitrile and any mixtures thereof in the presence of a catalyst selected from the group consisting of acetic acid, hydrochloric acid, sulfuric acid, phosphoric acid and any mixtures thereof at the temperature range from about 10 to about 80° C. In one embodiment, the process is carried out in the solvent of ethanol in the presence of the catalyst of acetic acid at the temperature range of about 20 to about 70° C.

DETAILED DESCRIPTION

The present invention provides a process for the preparation of 1,3-diethyl 2-(2-methylhydrazinylidene)propanedioate by using 2-halo-substituted diethyl malonate.

In one aspect, the present invention provides a process for the synthesis of 1,3-diethyl 2-(2-methylhydrazinylidene) propanedioate by reacting a 2-halo-substituted diethyl malonate with methylhydrazine or the salt thereof. As used in the context of the present invention, the term "2-halo-substituted diethyl malonate" refers to a halo-substituted diethyl malonate that includes one or two halogen substituent(s) at carbon-2 position of the diethyl malonate. The halo-substituent can be any member of the halogen family, including fluorine, bromine, chlorine, iodine and combinations thereof. In case of two halogen substituent, they can be the same or different halogens.

In one embodiment, 2-substituted diethyl malonate is selected from the group consisting of diethyl 2-bromomalonate, diethyl 2,2-dibromomalonate, diethyl 2-chloromalonate, diethyl 2,2-dichloromalonate, and any mixtures thereof.

In another embodiment, 2-halo-substituted diethyl malonate is a mixture selected from the group consisting of: diethyl 2-bromomalonate and diethyl 2,2-dibromomalonate; diethyl 2-chloromalonate and diethyl 2,2-dichloromalonate; diethyl 2-bromomalonate and diethyl 2-chloromalonate; diethyl 2-bromomalonate and diethyl 2,2-dichloromalonate; diethyl 2,2-dibromomalonate and diethyl 2-chloromalonate; diethyl 2,2-dibromomalonate and diethyl 2,2-dichloromalonate; diethyl 2-bromomalonate and diethyl 2,2-dibromomalonate and diethyl 2-chloromalonate; diethyl 2-bromomalonate and diethyl 2,2-dibromomalonate and diethyl 2,2-dichloromalonate; diethyl 2-bromomalonate and diethyl 2-chloromalonate and diethyl 2,2-dichloromalonate; diethyl 2,2-dibromomalonate and diethyl 2-chloromalonate and diethyl 2,2-dichloromalonate; diethyl 2-bromomalonate and diethyl 2,2-dibromomalonate and diethyl 2-chloromalonate and diethyl 2,2-dichloromalonate.

In another aspect, the present invention provides a process for the preparation of 1,3-diethyl 2-(2-methylhydrazinylidene)propanedioate by reacting 2-halo-substituted diethyl malonate with methylhydrazine or the salt thereof in a solvent or without solvent. In one embodiment, the solvent is an organic solvent. In a further embodiment, the solvent is selected from the group consisting of methanol, ethanol, 1-propanol, isopropyl alcohol, acetonitrile and any mixtures thereof.

In another aspect, the present invention provides a process for the preparation of 1,3-diethyl 2-(2-methylhydrazinylidene)propanedioate by reacting 2-halo-substituted diethyl malonate with methylhydrazine or the salt thereof in the presence of a catalyst. In one embodiment, the catalyst belongs to organic acid group. In a further embodiment, the catalyst is selected from the group consisting of acetic acid, hydrochloric acid, sulfuric acid, phosphoric acid and any mixtures thereof.

In another aspect, the present invention provides a process for the preparation of 1,3-diethyl 2-(2-methylhydrazinylidene)propanedioate by reacting 2-halo-substituted diethyl malonate with methylhydrazine or the salt thereof at the temperature range from about 10 to about 80° C. In another embodiment, the process is carried out at the temperature range from about 20 to about 70° C.

In another aspect, the present invention provides a process for the preparation of 1,3-diethyl 2-(2-methylhydrazinylidene)propanedioate by reacting 2-halo-substituted diethyl malonate with methylhydrazine or the salt thereof in a solvent selected from the group consisting of the methanol, ethanol, 1-propanol, isopropyl alcohol, acetonitrile and any mixtures thereof of a catalyst selected from the group consisting of acetic acid, hydrochloric acid, sulfuric acid, phosphoric acid and any mixtures at the temperature range from about 10 to about 80° C.

In one embodiment, 2-halo-substituted diethyl malonate is selected from the group consisting of: diethyl 2-bromomalonate, diethyl 2,2-dibromomalonate, diethyl 2-chloromalonate and diethyl 2,2-dichloromalonate, and any mixtures thereof. In a further embodiment, 2-halogenated diethyl malonate is a mixture selected from the group consisting of: diethyl 2-bromomalonate and diethyl 2,2-dibromomalonate; diethyl 2-chloromalonate and diethyl 2,2-dichloromalonate; diethyl 2-bromomalonate and diethyl 2-chloromalonate; diethyl 2-bromomalonate and diethyl 2,2-dichloromalonate; diethyl 2,2-dibromomalonate and diethyl 2-chloromalonate; diethyl 2,2-dibromomalonate and diethyl 2,2-dichloromalonate; diethyl 2-bromomalonate and diethyl 2,2-dibromomalonate and diethyl 2-chloromalonate; diethyl 2-bromomalonate and diethyl 2,2-dibromomalonate and diethyl 2,2-dichloromalonate; diethyl 2-bromomalonate and diethyl 2-chloromalonate and diethyl 2,2-dichloromalonate; diethyl 2,2-dibromomalonate and diethyl 2-chloromalonate and diethyl 2,2-dichloromalonate; diethyl 2-bromomalonate and diethyl 2,2-dibromomalonate and diethyl 2-chloromalonate and diethyl 2,2-dichloromalonate. In another embodiment, the process is carried out in the solvent of ethanol or acetonitrile in the presence of the catalyst of acetic acid at the temperature range from about 20 to about 70° C.

In another aspect, the present invention provides a process of the preparation of 1,3-diethyl 2-(2-methylhydrazinylidene)propanedioate by reacting 2-halo-substituted diethyl malonate with methylhydrazine or the salt thereof in a solvent selected from ethanol or acetonitrile in the presence of the catalyst of acetic acid at the temperature range from about 20 to about 80° C. In another embodiment, the reaction temperature range is 20 about to about 70° C. In a further embodiment, the process is carried out by adding 2-halogenated diethyl malonate to methylhydrazine dropwise.

The material 2-halogenated malonate can be easily obtained by reacting malonate with the corresponding halogen. The preparation of 2-halogenated malonate is well known to a person skilled in the art and has been described in many previous documents. For example, Organic Syntheses, Volume 7, Page 34 (1972) described a process for the preparation of bromo-malonate by reacting diethyl malonate with bromine. JP27004157 (1952) described a process for the preparation of diethyl 2,2-dibromomalonate by reacting diethyl malonate with bromine. The preparation of chloromalonate was described for example in Russian Journal of Applied Chemistry (Zhurnal Prikladnoi Khimii) (1985), 58(11), 2504-8, and the patent documents like US2008114196A1 and DE102006053380, where chloromalonate was prepared by reacting diethyl malonate with chlorine. All these previous disclosures are hereby incorporated by reference in its entirety.

The present invention is further illustrated by the following examples. These examples serve merely to illustrate particular embodiments of the invention and are not intended to limit the scope of the invention in any way. Further modifications encompassed by the disclosed invention will be apparent to those skilled in the art. All such modifications are deemed to be within the scope of the invention as defined in the present specification and claims.

EXAMPLES

Example 1—Preparation of DMP Using Cl-DEM

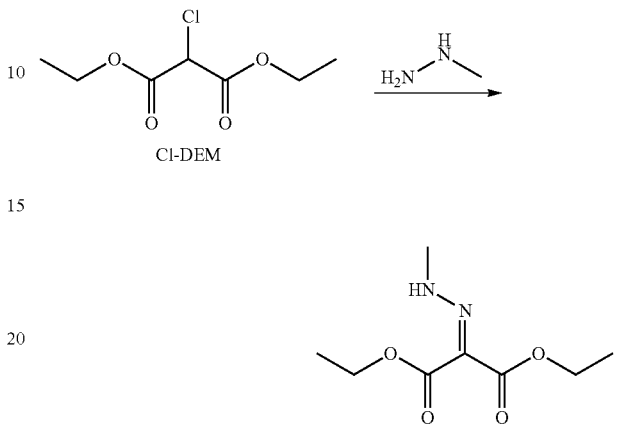

9.9 g of diethyl 2-chloromalonate was dissolved in 50 g of acetonitrile. The reaction solution was heated to 60° C. 13.3 g of 41% methylhydrazine was added into the solution drop-wise at 60° C. during-reflux. The reaction was monitored by gas chromatography (the "GC"). After the reaction was completed (the remained diethyl 2-chloromalonate in the reaction <1%, determined by gas chromatography) in 4 hours, water and toluene was added to extract the product. The toluene phase was concentrated to give 8.3 g of diethyl 2-(2-methylhydrazono)malonate as an oil. The purity is 71.3%. The yield is 58.6%.

Example 2—Preparation of DMP Using diBr-DEM

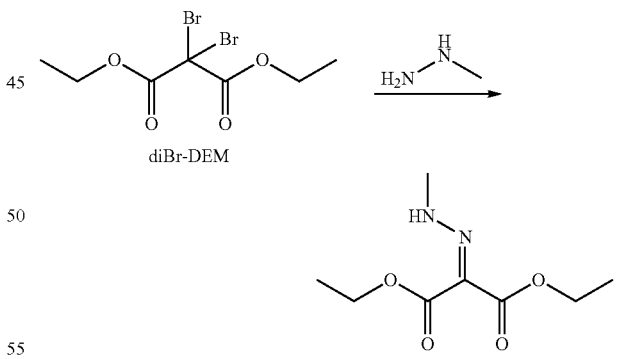

13.6 g of 41% methylhydrazine was dissolved in 13.6 g of ethanol. 13.2 g of diethyl 2,2-dibromomalonate was added into the solution drop-wise at 20-40° C. The reaction was monitored by GC. After the reaction was completed (the remained diethyl 2,2-dibromomalonate in the reaction <1%, determined by gas chromatography) in 6 hours, water and toluene was added to extract the product. The toluene phase was concentrated to give 7.7 g of diethyl 2-(2-methylhydrazono)malonate as an oil. The purity is 81.6%. The yield is 77.7%.

Example 3—Preparation of DMP Using Br-DEM

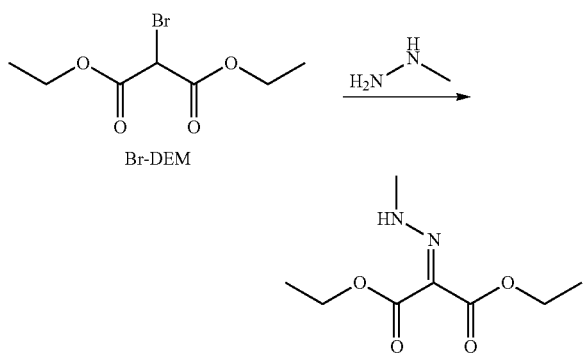

11 g of 41% methylhydrazine was dissolved in a mixture of 30 g of ethanol and 1.2 g of acetic acid. 10 g of diethyl 2-bromomalonate was added into the solution dropwise at 50-60° C. The reaction was monitored by GC. After the reaction was completed (diethyl 2-bromomalonate <1%, determined by gas chromatography) in 2 hours, water and toluene was added to extract the product. The toluene phase was concentrated to give 8.5 g of diethyl 2-(2-methylhydrazono)malonate as an oil. The purity is 74.5%. The yield is 78.9%.

Example 4—Preparation of DMP Using the Mixture of Br-DEM and diBr-DEM

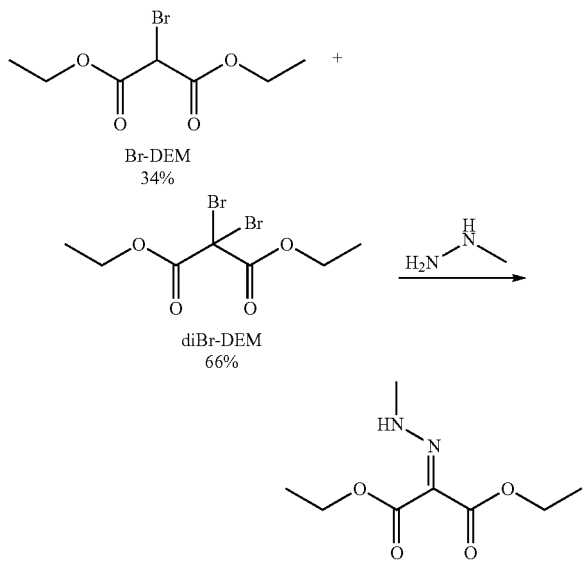

11.3 g of 41% methylhydrazine was dissolved in a mixture of 15 g of ethanol and 1.0 g of acetic acid. 9.7 g mixture of diethyl 2-bromomalonate (34%) and diethyl 2,2-dibromomalonate (66%) was added into the solution dropwise at 58-70° C. The reaction was monitored by GC. After the reaction was completed (diethyl 2-bromomalonate <1%, determined by gas chromatography) in 1 hour, water and toluene was added to extract the product. The toluene phase was concentrated to give 6.8 g of diethyl 2-(2-methylhydrazono)malonate as an oil. The purity is 75.05%. The yield is 75.5%.

While this invention has been described with an emphasis upon preferred embodiments, it will be obvious to those of ordinary skill in the art that variations in the preferred compositions and methods can be used and that it is intended that the invention can be practiced otherwise than as specifically described herein. Accordingly, this invention includes all modifications encompassed within the spirit and scope of the invention as defined by the claims that follow.

What is claimed is:

1. A process for the preparation of 1,3-diethyl 2-(2-methylhydrazinylidene)propanedioate, comprising the step of: reacting 2-halosubstituted diethyl malonate with methylhydrazine or a salt thereof optionally in the presence of an acid catalyst.

2. The process according to claim 1, wherein the 2-halo-substituted diethyl malonate is selected from the group consisting of diethyl-2-bromomalonate, diethyl-2,2-dibromomalonate, diethyl-2-chloromalonate, diethyl-2,2-dichloromalonate, and mixtures thereof.

3. The process according to claim 1, wherein 2-halo-substituted diethyl malonate is a mixture selected from the group consisting of: diethyl-2-bromomalonate and diethyl 2,2-dibromomalonate; diethyl-2-chloromalonate and diethyl-2,2-dichloromalonate; diethyl-2-bromomalonate and diethyl-2-chloromalonate; diethyl-2-bromomalonate and diethyl-2,2-dichloromalonate; diethyl-2,2-dibromomalonate and diethyl-2-chloromalonate; diethyl-2,2-dibromomalonate and diethyl-2,2-dichloromalonate; diethyl-2-bromomalonate and diethyl-2,2-dibromomalonate and diethyl-2-chloromalonate; diethyl-2-bromomalonate and diethyl-2,2-dibromomalonate and diethyl-2,2-dichloromalonate; diethyl-2-bromomalonate and diethyl-2-chloromalonate and diethyl-2,2-dichloromalonate; diethyl-2,2-dibromomalonate and diethyl-2-chloromalonate and diethyl-2,2-dichloromalonate; diethyl-2-bromomalonate and diethyl-2,2-dibromomalonate and diethyl-2-chloromalonate and diethyl-2,2-dichloromalonate.

4. The process according to claim 1, wherein the reacting step is carried out in a solvent selected from the group consisting of: methanol, ethanol, 1-propanol, isopropyl alcohol, acetonitrile and mixtures thereof.

5. The process according to claim 1, wherein the reacting step is carried out in the presence of an acid catalyst selected from the group consisting of: acetic acid, hydrochloric acid, sulfuric acid, phosphoric acid, and mixtures thereof.

6. The process according to claim 1, wherein the reacting step in carried out at the temperature range from 10 to 80° C.

7. A process for the preparation of 1,3-diethyl 2-(2-methylhydrazinylidene)propanedioate, comprising the step of: reacting 2-halo-substituted diethyl malonate with methylhydrazine or a salt thereof in a solvent selected from the group consisting of: methanol, ethanol, 1-propanol, isopropyl alcohol, acetonitrile and mixtures thereof, in the presence of a catalyst selected from the group consisting of acetic acid, hydrochloric acid, sulfuric acid, phosphoric acid and mixtures thereof, and at a temperature ranging from about 10 to about 80° C.

8. The process according to claim 7, wherein the reacting step is carried out in ethanol in the presence of acetic acid at the temperature range of from 20 to 70° C.

9. The process according to claim 7, wherein 2-halo-substituted diethyl malonate is a mixture selected from the group consisting of: diethyl-2-bromomalonate and diethyl 2,2-dibromomalonate; diethyl-2-chloromalonate and diethyl-2,2-dichloromalonate; diethyl-2-bromomalonate and diethyl-2-chloromalonate; diethyl-2-bromomalonate and diethyl-2,2-dichloromalonate; diethyl 2,2-dibromomalonate and diethyl 2-chloromalonate; diethyl-2,2-dibromomalonate and diethyl-2,2-dichloromalonate; diethyl-2-bromomalonate and diethyl-2,2-dibromomalonate and diethyl-2-chloromalonate; diethyl-2-bromomalonate and diethyl-2,2-dibromomalonate and diethyl-2,2-dichloromalonate; diethyl-2-bromomalonate and diethyl-2-chloromalonate and diethyl-2,2-dichloromalonate; diethyl-2,2-dibromomalonate and diethyl-2-chloromalonate and diethyl-2,2-dichloromalonate; diethyl-2-bromomalonate and diethyl-2,2-dibromomalonate and diethyl-2-chloromalonate and diethyl-2,2-dichloromalonate.

10. The process according to claim 7, wherein the process is carried out by adding 2-halo-substituted diethyl malonate to methylhydrazine dropwise.

11. The process according to claim 1, wherein the reacting step is carried out at the temperature range from 20 to 70° C.

12. The process according to claim 1, wherein the reacting step is carried out in a solvent selected from the group consisting of: methanol, ethanol, 1-propanol, isopropyl alcohol, acetonitrile and mixtures thereof at the temperature range from 10 to 80° C.

13. The process according to claim 12, wherein the reacting step is carried out in ethanol in the presence of acetic acid.

* * * * *